United States Patent [19]

Tarjan

[11] 4,419,996
[45] Dec. 13, 1983

[54] CARDIAC PACER APPARATUS

[75] Inventor: Peter P. Tarjan, Miami, Fla.

[73] Assignee: Cordis Corporation, Miami, Fla.

[21] Appl. No.: 243,135

[22] Filed: Mar. 12, 1981

[51] Int. Cl.³ .............................................. A61N 1/36
[52] U.S. Cl. ............................................ 128/419 PG
[58] Field of Search ......................... 128/419 PG, 644

[56] References Cited

U.S. PATENT DOCUMENTS

| 3,518,997 | 7/1970 | Sessions | 128/419 PG |
| 3,542,010 | 11/1970 | Love | 128/644 |
| 3,557,796 | 1/1971 | Keller, Jr. et al. | 128/419 PG |
| 4,091,817 | 5/1978 | Thaler | 128/419 PG |
| 4,203,447 | 5/1980 | Keller, Jr. | 128/419 PG |
| 4,307,725 | 12/1981 | Sowton et al. | 128/419 PG |

OTHER PUBLICATIONS

Kappenberger et al., Publication from Guy's Hospital, London, U.K. "Long Term Programmed Stimulation in Patients with Tachycardia".

Primary Examiner—William E. Kamm
Attorney, Agent, or Firm—Kenway & Jenney

[57] ABSTRACT

The pacing system disclosed herein involves both an implantable, battery-powered heart stimulating unit and an external, patient-operable overdriver unit. Responsive to the application of the external unit, the implanted unit switches from an inhibit mode to a synchronous mode in which it is responsive to and tracks signals generated by the external unit thereby to apply externally selectable stimulation sequences for the treatment of tachycardia-type arrhythmias.

12 Claims, 7 Drawing Figures

CARDIAC PACER APPARATUS

BACKGROUND OF THE INVENTION

The present invention relates to a cardiac pacing system and more particularly to a system useful in treating both bradycardia and tachycardia type arrhythmias.

In certain patients, particularly those suffering from sinus node disease, the basic atrial action of the heart may exhibit arrhythmias of both the bradycardia and tachycardia types. Often, the hearts of such patients beat essentially normally with only occasional lapses in bradycardia, in which the heart beats too slowly to effect adequate blood circulation. Occasionally, however, the hearts of such patients will break into tachycardia where the heart beats at too high a rate. While some such tachycardia attacks may revert spontaneously or in response to pharmacologic treatment, other types may persist for almost indefinite periods which are very debilitating to the patient. Certain other patients suffer from periodic ventricular tachyarrhythmias which do not respond to medical treatment.

Among the several objects of the present invention may be noted the provision of atrial pacing apparatus which is useful in treating both bradycardia type and tachycardia type arrhythmias; the provision of such apparatus in which the initiation of a stimulating sequence appropriate for the treatment of tachycardia may be initiated by the patient; the provision of such a system in which a particular sequence of stimulations for treating tachycardia may be externally predetermined; the provision of such a pacing system which incorporates an implantable pacer which is itself effective in treating bradycardia type arrhythmias; the provision of such apparatus which is easy to use, is highly reliable, and is of relatively simple and inexpensive construction. Other objects and features will be in part apparent and in part pointed out hereinafter.

SUMMARY OF THE INVENTION

Briefly, a cardiac pacing system according to the present invention involves both an implantable, battery-powered stimulating unit and an external patient-operable overdriver unit. The implantable unit is operable in a first mode to provide, on its own, inhibit mode pacing suitable for treating bradycardia type arrhythmias. Upon application of the external unit, which in a preferred implementation may be sensed by means of a magnet included in the overdriver, the implanted unit switches to a synchronous mode in which it is responsive to control signals generated by the overdriver unit. The overdriver unit generates these control signals in a pattern preselectable by the treating physician so as to effect a corresponding pattern of stimulating pulses to be applied to the patient's heart for the treatment of tachycardia type arrhythmias.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
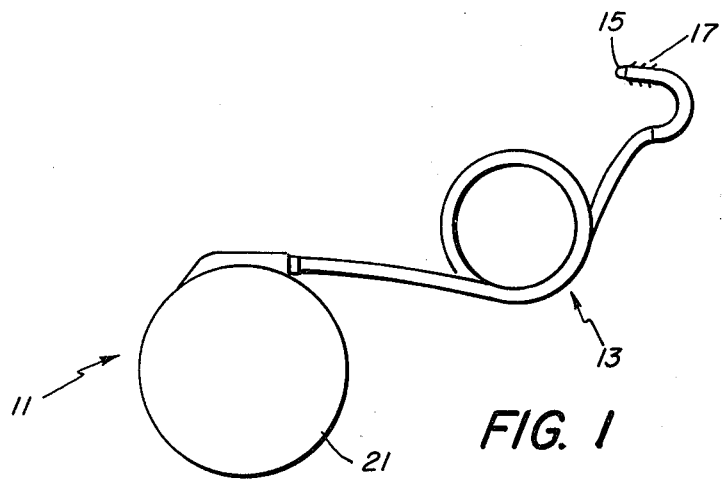
FIG. 1 is a view illustrating the physical arrangement of an implantable stimulating unit employed in a system of the present invention with a pervenous lead attached.

Referring now to FIG. 1, the stimulation unit illustrated is battery powered and is adapted to be completely implanted. The implanted unit comprises the pacer package itself designated by reference character 11, and a flexible lead 13. The particular unit illustrated is adapted for pervenous installation in which the pacer package 11 is implanted in a subcutaneous pocket formed in the patient's chest near his shoulder, the lead 13 being threaded through a vein to the patient's heart. Lead 13 is provided at a distal end with a conductive tip or electrode 15 suitable for stimulating the heart. The distal end may be shaped to facilitate placement within the atrium and may incorporate projections, as indicated at 17, which engage trabeculae within the heart so as to facilitate retention of the lead in the proper position.

The pacer package 11 comprises a hermetically sealed metal can 21 containing stimulation electronics and pulse generating electronics and batteries for powering the electronic circuitry. An electrical feedthrough (not shown) provides a connection through the can wall to a connector which is formed in an insulating neck 22 extending from one side of the can 21. A plug on the proximal end of lead 13 is received in the socket for establishing electrical connection between the pulse generating circuitry and the stimulating electrode 15. As is conventional, the outer surface of the can 21 forms the reference or ground electrode, the lead 13 being of the unipolar type.

As is explained in greater detail hereinafter, the implantable stimulator of FIG. 1 is responsive to the presence of the field of a permanent magnet for switching from an inhibit mode of operation to a synchronous mode in which externally applied electrical signals can control the generation of stimulating pulses. In the inhibit mode, the implanted pacer is principally responsive to naturally occurring heartbeat signals. Only when the time between such signals exceeds a preselected value does the implanted device generate a stimulating pulse.

Figure 2:
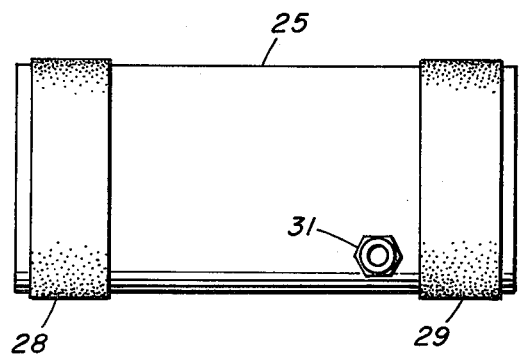
FIG. 2 is a view illustrating the physical arrangement of an external overdriver which can be employed in cooperation with the implantable pacer of FIG. 1 in the practice of the present invention.

In accordance with the present invention, a mode switching magnetic field and suitable control signals are provided by an external, patient-operable unit which is integrated in physical form so as to be readily applied and operated by the patient himself. The physical arrangement may be seen in FIGS. 2 and 3. An insulating plastic housing 25 encloses both a permanent magnet 27 for effecting mode switching and electronics for generating control pulses, together with a suitable battery.

Figure 3:
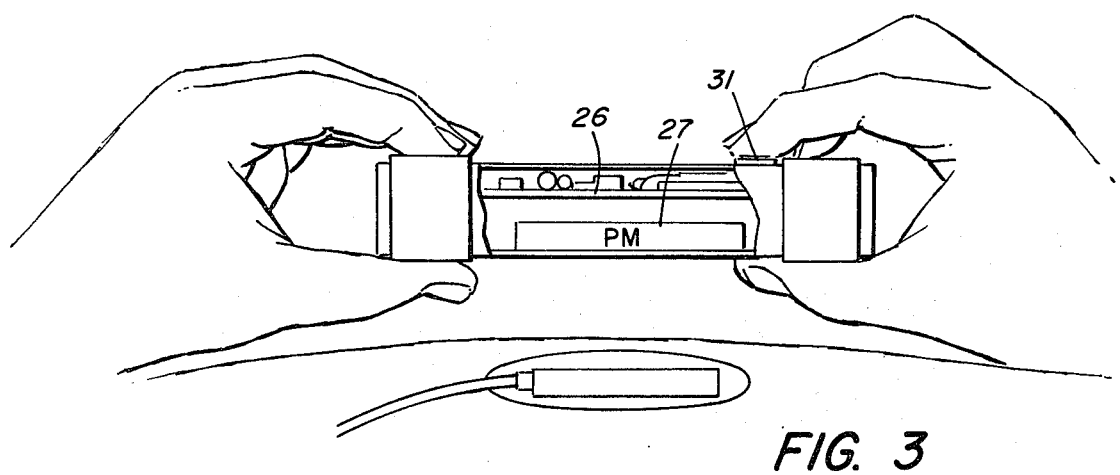
FIG. 3 is a view, with portions shown in section, illustrating the manner in which the external overdriver of FIG. 2 may be applied by a patient to interact with the implanted stimulating unit.

The electronics may, as illustrated, be assembled on a circuit board, designated generally by reference character 26 in FIG. 3. Finger-contacting electrodes are provided at each end of the housing 25, as indicated at 28 and 29. Electrodes 28 and 29 are preferably formed of a commercially available Velcro material made with metallic thread. This material has been found to reliably form a low resistance contact when gripped by a patient. A pushbutton 31 for initiating operation of the circuitry is located adjacent the electrode 29 so as to be easily operated by a finger of the same hand which is gripping the electrode 29.

FIG. 3 illustrates the manner in which the patient can apply the external device to effect treatment of tachycardia arrhythmias. Holding the external device with one hand gripping each of the electrodes 28, 29, the patient positions the external device over the implanted stimulator so that the field from the permanent magnet 27 operates the mode switching element in the pacer package. Typically, this element will be a magnetic reed switch as is conventionally used for signalling in the pacer art. By then pressing the pushbutton 31, the patient causes the overdriver circuitry to generate a predetermined sequence of control pulses between the electrodes 28 and 29. Through the finger contacts 28 and 29, a conductive path is established between the electrodes 28 and 29 which links the patient's chest so that the pulses can be sensed by the implanted stimulation unit. In other words, a portion of the control pulse potential will appear between the electrode 15 and the pacer case 21. Typically, it will be useful to observe proper polarity in terms of which hand grasps which electrode so as to assure reliable sensing.

In addition to providing a connection which allows control pulses generated by the overdriver to be coupled to the implanted device, the finger electrodes 28 and 29 can also be employed to allow the overdriver circuitry to sense signals generated from within the patient's body. While it would be difficult to sense the natural EKG signal in this manner, pulse signals generated by the implanted pacer are relatively easily detected, both because of their amplitude and their pulse-like waveform. This sensing capability is utilized in one version of the overdriver as described in greater detail hereinafter.

Figure 4:
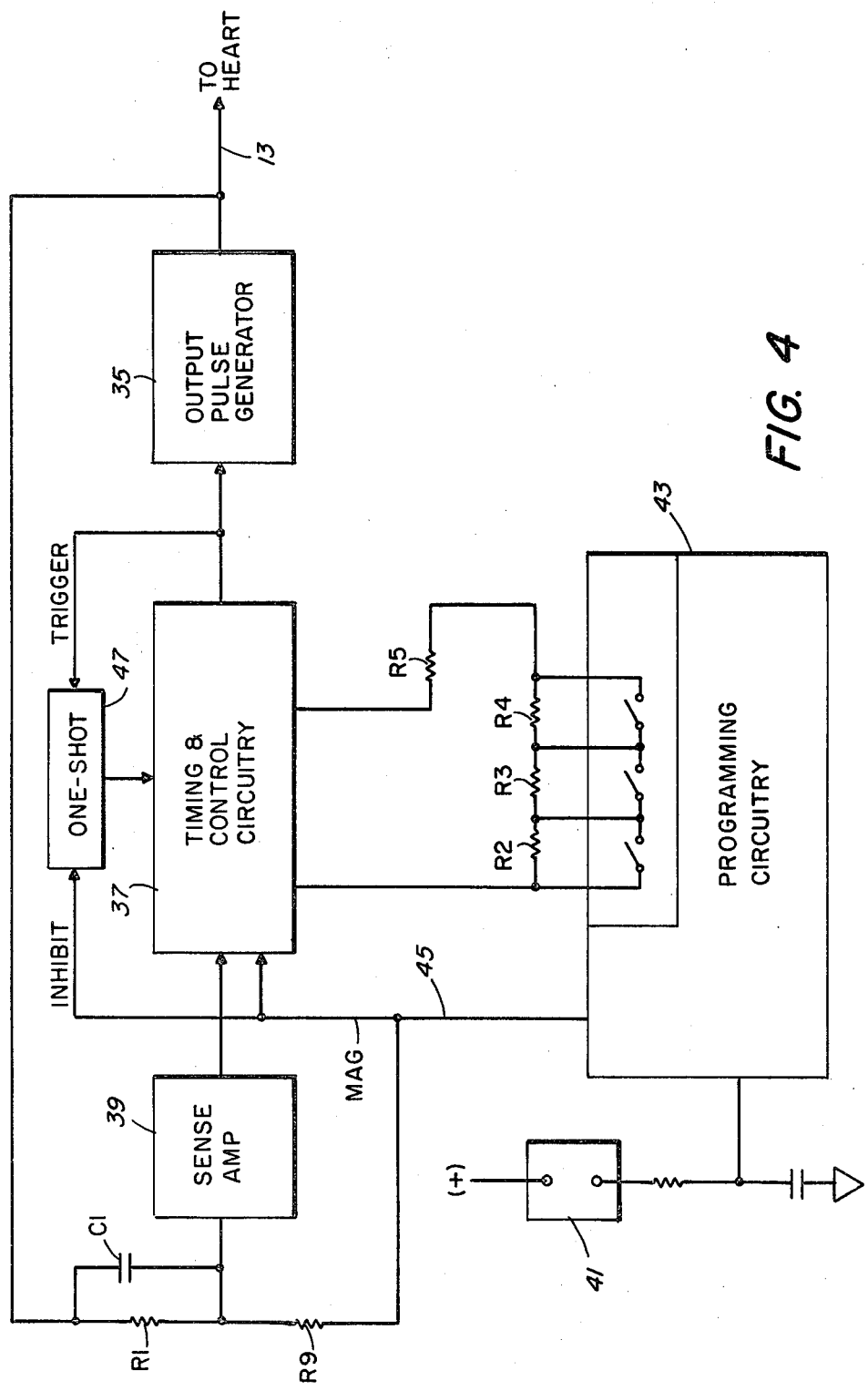
FIG. 4 is a block diagram of circuitry employed in the implantable stimulating unit of FIG. 1.

The general arrangement of the circuitry employed in the implantable stimulating unit of FIG. 1 is illustrated in FIG. 4. Pulses of an amplitude suitable for stimulating cardiac tissue are selectively generated by a conventional output pulse generator 35 upon initiation by timing and control circuitry 37. For application to the heart, these output pulses are coupled to the pervenous lead 13. As is understood by those skilled in the art, naturally occurring cardiac signals can be sensed through this same pervenous lead. For this purpose, the lead 13 is connected also to the input terminal of a sense amplifier 39 through a simple input network comprising a resistor R1 shunted by a capacitor C1.

The timing and control circuitry 37 is preferably of the digital type dischosed in U.S. Pat. No. 3,557,796 and comprises a digital counting chain drive by an oscillator operating at a frequency which is a relatively large multiple of a normal heartbeat rate. The timing and control circuitry 37, while similar in certain respects to that employed in previously known inhibit and synchronous mode pacemakers, is modified in certain respects in accordance with the present invention. These modifications are therefore described in greater detail hereinafter. Preferably also, the oscillator frequency is programmable as described in U.S. Pat. No. 3,805,796. In the particular embodiment illustrated, the oscillator's frequency is adjustable by means of an external resistance comprising a series of resistors R2–R5, selective ones of which may be controllably shorted by semiconductor switches so as to effectively vary the operative resistance in the oscillator circuit.

Programming is effected by repetitively operating a magnetically sensitive reed switch 41 at a rapid rate so as to generate an enable code and a programming sequence, again as described in U.S. Pat. No. 3,805,796. The circuitry for performing this sort of programming function is known in the art and is not described in detail herein but is represented generally by block 43. This circuitry also includes elements for conditioning the signal generated by the reed switch and determining whether the reed switch is in a steady state closed condition or is being pulsed in accordance with the predetermined programming sequence. If the reed switch is pulsed in accordance with the proper predetermined code, selected ones of the semiconductor switches are closed to cause the oscillator to operate at the desired rate. The switches are indicated along the upper portion of the block 43. If the reed switch 41 closes and stays closed, a digital output line 45 is asserted. Hereinafter, this signal is designated MAG. In many prior art pacers, this signal is employed to switch the pacing control circuitry from an inhibit or synchronous mode to an asynchronous mode for checking the basic escape interval of the apparatus. This procedure is conventionally known as determining the "magnet rate" of the pacer. Often this rate is used as means of determining battery condition, the magnet rate being a controlled variable of battery voltage. In accordance with the present invention, however, this signal is employed to change the mode of the pacer from an inhibit mode to a special form of synchronous mode, again as described in greater detail hereinafter.

In addition to changing the mode of the timing and control circuitry 37, the magnet signal can also reduce the sensitivity of the sense amplifier by shunting its input through a resistor R9. Whether this reduction in sensitivity is desired or not depends on the particular therapeutic sequence which is to be implemented by the external overdriver. In the following portions of the specification two different overdriver schemes are described, one of which may utilize the reduction in sensitivity and the other of which does not.

While the timing and control circuitry 37 incorporates digitally timed means which determine a minimum refractory period, the device of FIG. 4 also employs a separate and redundant circuit for establishing an operative refractory period during inhibit mode pacing. This is a one-shot multivibrator, i.e. an analog timing circuit, as indicated at 47 in FIG. 4. The refractory one-shot 47 is triggered by the application of a control pulse from the control circuitry 37 to the output pulse generator 35 and the one-shot in turn generates an output signal which is applied to the control circuitry for defining the end of the refractory period. This separate circuit also, by its nature, establishes a rate limit which is independent of the digital timing circuit.

Figure 5:
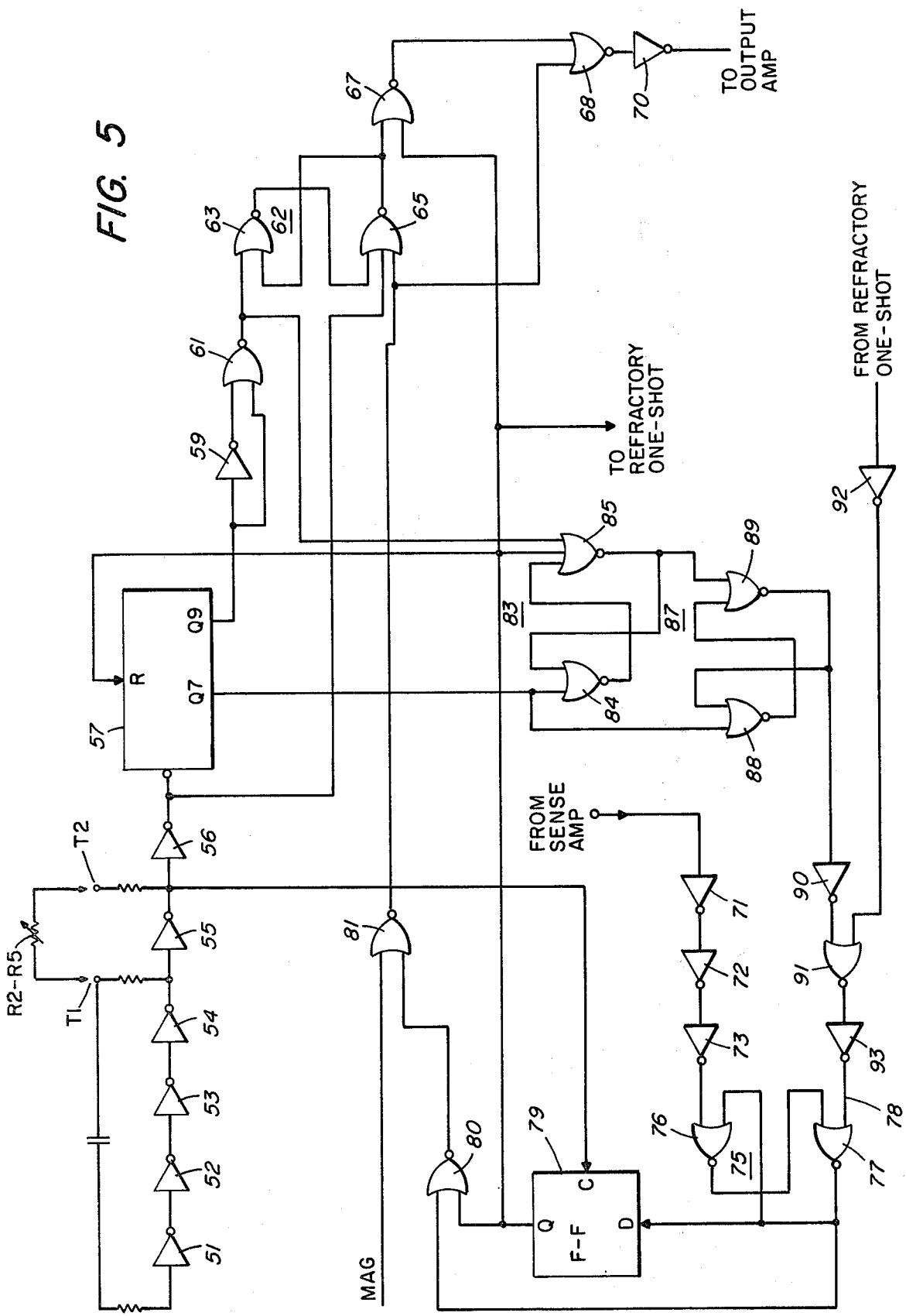
FIG. 5 is a logic diagram illustrating in greater detail timing and control circuitry which is part of the circuitry of FIG. 4.

Referring now to FIG. 5, the circuitry illustrated there is preferably implemented as a C-MOS integrated circuit. In one particular embodiment of the invention, the required digital elements were obtained using portions of an already designed C-MOS pacer chip. Different interconnections between the elements were then implemented by changing the last metalization step. The basic chip was the so-called alpha timing chip employed in Cordis Omnicor pacers.

The oscillator described earlier comprises five inverters 51–55. The oscillator frequency is adjustable by varying the resistance value (R2–R5) connected between terminals T1 and T2. Through a buffer inverter 56, the oscillator drives a ninestage binary counter 57. The output from the last stage of the counter, designated Q9, is applied to a falling edge detector comprising an inverter 59 and a lower gate 61.

The brief pulse generated by the falling edge detector is applied to selectively set a flip flop 62 comprising a pair of NOR gates 63 and 65. At the end of one clock period, flip flop 62 can be reset by the clock signal which is applied as one input to the gate 65. In the inhibit mode of operation, this is the mechanism by which output pulses are timed. That is, an output pulse will be generated when the counter 57 reaches its highest value without being reset. In the inhibit mode, such pulses are passed through NOR gates 67 and 68, assuming that the other input to each of these gates is in the appropriate state, to an output buffer gate 70.

The output signal from the sense amplifier 39 (FIG. 4) is applied, through buffering gates 71–73, to set a flip flop 75 comprising a pair of NOR gates 76 and 77. This setting, however, can occur only when the input to gate 77 on line 78 is in a low state. This signal indicates the presence of a refractory period and is high during such periods. The flip flop 75 can be reset by a signal on line 78 which indicates that a refractory period has been initiated. As noted previously, this refractory signal can be derived from either of two sources, either the one-shot multivibrator 47 (FIG. 4) or a digitally timed refractory period as described in greater detail hereinafter.

The output signal from gate 77 is applied to the data input of a D-type flip flop 79 which is clocked directly from the oscillator. The output signal from the D-type flip flop 79 which is considered to be a "clocked sense" signal, is applied as one input to a NOR gate 80 while the direct output from the sense flip flop 75 is applied as the other input to this gate.

The output signal from gate 80 is a negative going pulse when a sensed signal is sensed by the sense amp during a nonrefractory period, i.e., during an alert state. This signal is applied as one input to a NOR gate 81. The other input to this gate is the mode control (MAG) signal. Thus, the sense pulse will be passed by gate 81, in inverted form, only when the reed switch 41 is open. When the device is in its synchronous mode, the output from gate 81 is always low. The output signal from gate 81 is applied as the third input to gate 65, described previously, and to the last gate 68 in the output signal chain.

The clocked sense pulse, i.e., the output signal from D-type flip flop 79, is also applied as a reset signal to the timing counter 57 and as a reset signal to a flip flop 83 comprising a pair of NOR gates 84 and 85. Flip flop 83 is set by the output from the seventh state of the counter 57, i.e. at a count of 64. The same signal sets a second flip flop 87 which comprises NOR gate 88 and 89. Flip flop 87 can be reset by the output from flip flop 83. Flip flop 83 can be reset by either the "clocked sense" signal from D-type flip flop 79 or by the falling edge detector, the output signal from gate 61.

The output signal from gate 89 is taken as a digitally timed refractory period for the implantable device, a signal which is asserted for counts zero through 64 is then unasserted for the rest of the complete cycle of the counter. After passing through a buffering inverter 90, this signal is applied as one input to the NOR gate 91. The other input to this gate is a signal derived from the one-shot multivibrator 47. It can thus be seen that either of the signals can pull low the output of gate 91, and through inverter 93 assert a logical high on line 78.

The operation of the timing and control circuitry 37 in the two modes, inhibit and synchronous, is as follows:

In the inhibit mode, a sensed, heartbeat occurring after the refractory period will, at the next clock cycle, cause the output from D-type flip flop 79 to go high. This signal resets the counter 57, thereby restarting the escape interval, and resets the flip flops 83 and 87. Though a falling edge may be generated out of the last stage of the counter 57, no output pulse will be generated since the positive going output signal obtained from gate 81 will block any output from the gate 68. The resetting of the counter 57 and the flip flops 83 and 87 also initiates the refractory timing circuitry which inhibits further sensing until the count of 64 is reached and until the one-shot multivibrator 47 times out. After these refractory periods time out and the circuitry is in its "alert" state, sensed naturally occurring heartbeats can again reset the counter Thus, so long as naturally occurring heartbeats are sensed more often than the time required to cycle the counter 57, no stimulating pulses will be generated. The actual time required for this complete cycle will, of course, depend upon the frequency of the oscillator which is preferably programmable, as referenced earlier, so as to establish a suitable range of escape intervals or minimum heartbeat rates. Thus, in this mode, the implanted pacer is suitable for treating arrhythmias of the bradycardia type.

In the synchronous mode, where the output of gate 81 is held low by the MAG signal, the gate 68 does not block possible output signals. Such output signals can be generated in either of two ways. From the count of 256 to 512, the falling edge detector will generate an output pulse as described previously. However, even in the preceding 64 counts, an output signal can be generated in response to a signal sensed by the input amplifier 39 by the "clocked sense" signal, i.e. the output from D-type flip flop 79 which is applied as the second input to the gate 67. The reset signal is, in either case, applied to trigger the one-shot multivibrator 47 and initiate its refractory timing interval. As indicated previously, when the device is in this synchronous mode, it will slave to an external device which generates, through the patient's body, a sufficient electrical signal to be picked up by the sense amp 39.

Figure 6:
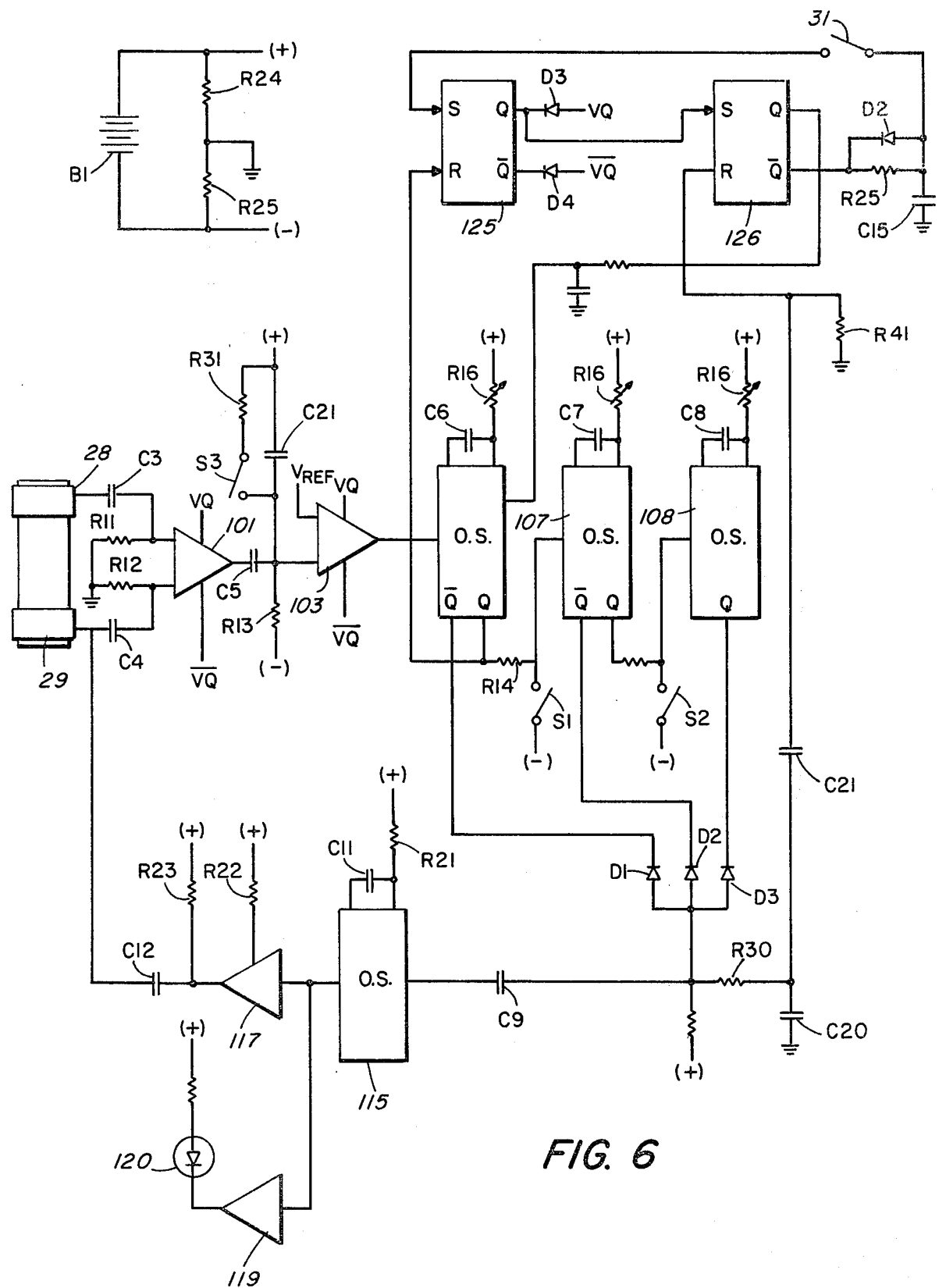
FIG. 6 is a block diagram of one type of circuitry which may be employed in the overdriver of FIG. 2.

In the embodiment of the overdriver illustrated in FIG. 6, the psssible reduction in sensitivity in the implanted device is not utilized. Rather, this version of the overdriver utilizes the synchronism of implanted device output with naturally occurring heart signals to establish a desired time relationship or phasing of subsequent stimulation pulses in relation to the last occurring natural heartbeat. The particular embodiment illustrated can cause one, two or three stimulating pulses to be issued following a naturally occurring heartbeat, with the delay to each stimulating pulse being individually controlled.

Referring now to FIG. 6, it can be seen that the finger contact electrodes 28 and 29 are connected, through coupling capacitors C3 and C4, to respective input terminals of a differential input, instrumentation amplifier 101. A nominal d.c. ground potential is maintained at each of these inputs by resistors R11 and R12. The output signal from amplifier 101 is a.c. coupled, through a capacitor C5, to one input of a comparator 103. This input is maintained at a nominal negative potential through resistor R13. A preselected reference voltage is applied to the other input of the comparator.

The output from comparator 103 is applied to trigger a first one-shot multivibrator 106. Through resistor R14, this first one-shot is connected to selectively trigger a second one-shot 107. In turn, this second one-shot is connected, through resistor R15, to selectively trigger a third one-shot 108. Sequential triggering of the second and third multivibrators, however, can be selectively inhibited by shunting the triggering signals, i.e. by closing switches S1 and S2 respectively. Each of the one-shot multivibrators 106, 107, and 108 is provided with an RC timing network comprising capacitors C6-C8 respectively, and variable resistors R16-R18 respectively. Thus, the time interval of each of these one-shot multivibrators may be adjusted independently of the others. The presently preferred range of adjustment is 175 to 425 miliseconds.

Output signals from the three multivibrators 106-108 are combined in a diode array D1-D3. The output signal from the diode array will thus be low during each of the three timing intervals. It will, however, exhibit a brief positive-going pulse at the end of each timing interval. These positive-going pulses are coupled, through a capacitor C9 to selectively trigger. The period determining components of one-shot 115, capacitor C11 and resistor R21 are selected to provide a relatively short output pulse, i.e. in the order of two milliseconds. One shot 115 drives a current controlled switching amplifier 17 which applies, through coupling capacitor C12, a corresponding current pulse to the finger electrode 29. The maximum output current which will be provided by amplifier 117 is adjusted by means of a variable resistor R22. The proper nominal potential is maintained at the output terminal of switching amplifier 117 by resistor R23 when the switch is in its off state. One shot 115 also drives an amplifier 119 connected to energize an LED (light-emitting diode) 120 in synchronism with the generation of output pulse to the finger electrode 29.

Positive and negative supply voltage are provided by a battery B1 with the nominal ground potential being established by a resistive voltage divider R24-R25. The various logic elements and one-shot multivibrators employed in this circuit are preferably constructed of low power C-MOS circuitry so that they may be left energized continuously without appreciable drain on the battery. Likewise the output switching amplifiers 117 and 119 draw appreciable power only during the brief output pulses and thus these elements may also be left energized. The instrumentation amplifier 101 and comparator 103, however, are preferably of bipolar construction and draw appreciable current whenever energized. Accordingly, to limit the energization of these elements to only the necessary time period, a power switching circuit is employed for selectively energizing these elements. This power switching circuit employs two S-R flip flops 125 and 126. These flip flops are preferably also of the C-MOS construction so as to themselves dissipate very little power internally.

Assuming that both flip flops 125 and 126 have been reset for some appreciable time, the capacitor C15 will have been charged through resistor R25. These values are chosen to provide a relatively long time constant. When capacitor C15 is charged, pressing the initiation pushbutton 31 will cause the flip flops 125 and 126 to be set. The Q and Q-bar outputs from flip flop 125 will then provide the positive (VQ) and negative (VQ-bar) supplies to the instrumentation amplifier 101 and the comparator 103. Diodes D3 and D4 prevent back biasing of these supplies. The output of comparator 103 is connected to selectively reset the flip flop 125. Flip flop 126 can be reset by the output of a low pass filter, comprising resistor R30 and capacitor C20, which is connected to the diode array. The filter removes the positive-going pulses described previously. As indicated previously, the output from the diode array will be low during the time interval of any one of the one shots 106-108. However, once all of these one shots have executed their timing interval, the output from the gate 111 will go to a steady logic high and the capacitor C20 will recharge, thus resetting the flip flop 126. Until the flip flop 126 is thus reset, further operations of the pushbutton 31 will have no effect on the circuitry, since the capacitor C15 will be discharged through diode D2.

In order to test the device, a test pushbutton S3 is provided for selectively triggering the comparator 103 and initiating a sequence of timing operation, independently of any sensed heartbeat. This provides to test of the timing circuitry. Thus, if switch 31 is closed and the switch S3 is then operated, the various timing intervals may be checked out.

In practice it is contemplated that only the initiation switch pushbutton 31 and the test switch S3 will be accessible to the patient. The switches S1 and S2, the interval adjusting resistances R16-R18 and the current output adjusting resistor R2 will be adjusted by the physician to affect the desired treatment sequence and then closed up inside the enclosure 25. Depending upon the nature of the patient's ailment and the philosophy of the treating physician, a sequence of one, two or three stimulating pulses may be selected and the pulses will follow a preselected time pattern initiated by a naturally occurring heartbeat. A sequence often found to be effective in treating certain tachycardia type arrhythmias is to issue two stimulation pulses following a sensed heartbeat.

As indicated previously, a naturally occurring heartbeat can be sensed relatively easily once the overdriver is in place, since each naturally occurring heartbeat will be accompanied by a synchronized output pulse from the implanted stimulation device 11. Accordingly, when the patient senses that he is experiencing a tachycardia type arrhythmia he can apply the overdriver as illustrated in FIG. 3 and operate the treatment initiation pushbutton 31. Once the pushbutton 31 is operated, the stimulation pulse accompanying the next naturally occurring heartbeat will be sensed by the amplifier 101 and its output pulse will in turn trigger the comparator 103. After a delay determined by the setting of resistance R16, the output one-shot 15 will be triggered applying a signal pulse to the finger electrode 29. This signal pulse will, in turn, be sensed by the implanted stimulation device 11 which will respond by immediately issuing stimulation pulse to the heart. Essentially simultaneously the second one-shot 107 in the overdriver will be triggered and, after its preselected delay, a second control signal will be applied through the finger electrode. The second control pulse will likewise trigger the generation of a stimulation pulse by the implanted device. If desired, a third stimulation pulse may be likewise indirectly elicited from the implanted unit 11 after a delay selectable by means of the third overdriver one-shot 108. As is understood by those skilled in the cardiology art, the application of stimulating pulses in the fashion can break up certain types of tachycardia type arrhythmias, assuming the intervals are appropriately chosen in relation to the heart's own beating pattern in the arrhythmia. This mode of operation thus effectively involves a signalling in both directions. The implanted device, in its synchronous mode, triggers the overdriver so that timing is started on the basis of a naturally occurring heartbeat and then the overdriver signals the implanted device to issue stimulation pulses in accordance with the predetermined pattern selected by the patient's physician.

Figure 7:
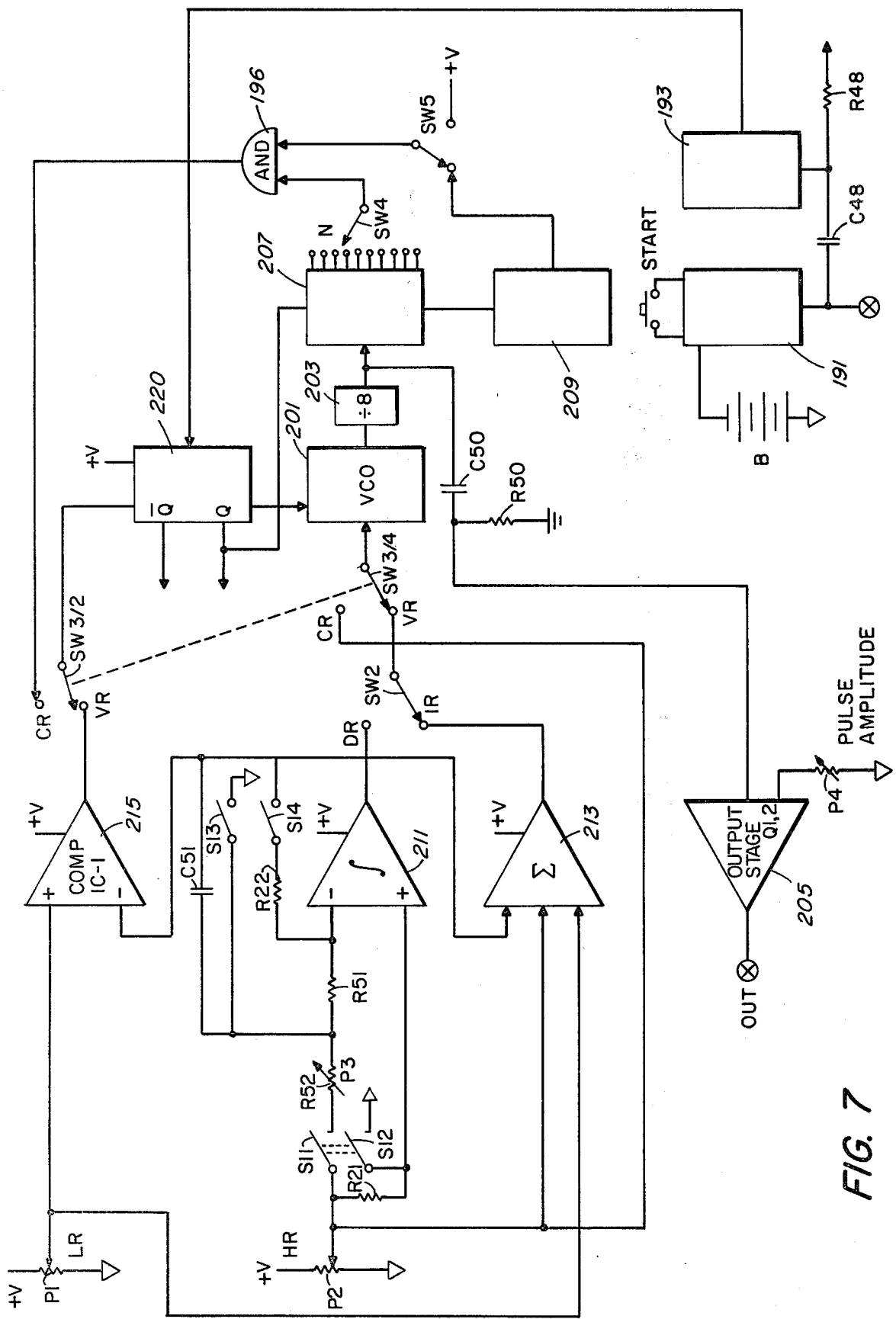
FIG. 7 is a block diagram of another type of overdriver circuitry.

The overdriver circuitry illustrated in FIG. 7 can provide a greater variety of different stimulation sequences and pattern than the device of FIG. 6 but it does not initially synchronize with a naturally occurring heartbeat. Thus, the implanted stimulation device used in connection with this overdriver is preferably provided with the gain reduction feature described previously. That is, the attenuating resistor R9 is included within the circuitry and is switched onto the sensing input of the implanted unit when the MAG signal is present. With this reduced sensitivity, the implanted stimulating unit is expected not to trigger on natural heart signals but will still sense and track control signals generated by the external overdriver.

The overdriver of FIG. 7 provides both a fixed rate mode of operation in which a preselected number of pulses are issued at a preselected rate or a scanning mode in which the rate at which pulses are issued is scanned at a preselectable speed between preselectable starting point and end point rates. Scanning can either be in an increasing or decreasing direction. Output pulse rate is controlled in the first instance by a voltage controlled oscillator 201. Oscillator 201 operates at a frequency which is eight times higher than the actual output pulse rate and this frequency is counted down by a divide-by-eight binary counter 203. The square-wave output signal from the divide-by-eight counter 203 is differentiated by a network comprising a capacitor C50 and resistor R50 to generate a short pulse of appropriate duration which is applied to a current controlled output amplifier 205. The output signal for this amplifier is applied to the finger electrode 29, just as in the embodiment of FIG. 6.

As in the previous embodiment, only certain portions of the overdriver circuitry are continuously energized and other portions are energized only during operation. Pressing the initiating pushbutton 31, triggers a one-shot multivibrator 191 which is one of the devices continuously energized. The Q output of this device controls the application of power to the other devices in the circuit. The period of one-shot 191 is selected to be about 20 seconds, a period which is long enough to allow the maximum preselectable number of pulses to be generated at the slowest preselectable rate. Triggering of one-shot 191 also, triggers a second one-shot 193 through a differentiating network comprising capacitor C48 and resistor R48. The one-shot 193 has a relatively short period, i.e. one-half a second, and provides a period during which the circuitry can stabilize and be initialized. Initialization is accomplished by means of an S-R flip-flop 220. When power is first applied, the flip-flop 220 assumes its reset state in which the Q output is logic high. After the delay provided by the multivibrator 193, the flip-flop 220 is set allowing the pulse generating circuit to operate in the manner selected. The generation of pulses continues until the flip-flop 220 is reset. The manner in which this resetting occurs differs between the two modes of operation. The fixed rate mode is described first.

The output signal from the divide-by-eight counter 302 is also applied to a decade counter 207 which is utilized in the fixed rate mode of operation of this apparatus. The carry signal from decade counter 207 is applied to a binary counting stage 209 to double the possible counting range. During the initialization state, the decade counter 207 and the binary counting stage 209 are reset and the voltage controlled oscillator is inhibited by the Q output from flip-flop 220. A pair of potentiometers P1 and P2 provide a pair of preselectable voltages representing corresponding rates of stimulation. These potentials are designated LR (low rate) and HR (high rate) for convenience in description. When this apparatus is operated in its fixed rate mode, the voltage HR is applied directly to the voltage controlled oscillator 201 as its control potential, through the switch SW3/1 (CR position).

At the end of the initialization period, the voltage controlled oscillator is released and will begin oscillating with a period determined by HR, in other words by the setting of potentiometer P2. For each eight cycles of the oscillator, an output pulse will be generated and applied to the finger electrodes.

The number of output pulses which are generated during a single sequence in the fixed rate mode is selected by appropriately setting the switches SW4 and SW5. The output signals obtained from the switches SW4 and SW5 are confined in an AND gate 196. In the fixed rate mode, the output of AND gate 196 is connected, through switch SW3/2, to the reset input of SR flip-flop 220. Thus, when the preselected count is reached, indicated by a logic high at both inputs to an AND gate 196, the flip-flop 220 is reset terminating the pulse generating operation.

In the scanning or variable rate mode, the control voltage for oscillator 201 is taken either directly from an integrator 211 or indirectly through a summing amplifier 213 which inverts the output from the integrator, this selection being made through switch SW2. For sensing the desired end of a scanning sequence, the output signal from the integrator 211 is also applied to comparator 215, where it is compared with the other pre-established potential (LR).

Integration is performed, in conventional manner, by linearly charging a capacitor C51 connected from the output of the integrating amplifier 211 to its inverting input, i.e. through resistance R51. The rate of charging during integration is controlled by an adjustable input resistor R52 which limits the charging current independently of the input voltage to the integrator.

In order to permit the rate scanning circuit to be initialized and then operated as a linear integrator, four switches S11–S14 are incorporated in the circuit. The switches are operated simultaneously by complimentary output signals taken from the control flip flop 220. When flip flop 220 is set, switches S13 and S14 are closed and switches S11 and S12 are open. This is the initializing mode during which the inverting input of the amplifier 211 is grounded and the voltage HR is applied to its non-inverting input. The closing of switch S14 causes the output voltage to follow the non-inverting input and accordingly capacitor C51 is charged to potential HR.

When the flip flop 220 is reset, the comlimentary condition prevails, the non-inverting input is grounded and the amplifier operates as an integrator. In this operation the output voltage on capacitor C51 decreases linearly at a rate determined by the setting of potentiometer R52. Linear integration continues until the voltage on the capacitor C51 reaches a level equal to voltage LR. At this point the comparator 215 will be triggered. With the switch SW3/2 in the variable rate position, the triggering of comparator 215 will cause the control flip flop 220 to be reset, thereby terminating the operation.

During the period of integration, the frequency of operation of the voltage controlled oscillator 201 is controlled by the output voltage of the integrator i.e., the voltage on capacitor C51. Accordingly, it can be seen that the pulse rate will be scanned linearly from a preselected high rate corresponding to the voltage HR to a preselected low rate corresponding to the voltage LR. The speed of scanning is also adjustable by means of variable resistance R52. Scanning in the opposite direction, i.e. from a low rate to a higher rate, may be obtained by operating switch SW2 to connect the input of the voltage controlled oscillator 201 to the output of the summing amplifier 213 rather than directly to the output of the integrator 211. The output signal from the integrator, designated DR, is applied as an input to the summing amplifier as are the two limit voltages HR and LR. Summing amplifier generates a voltage, designated IR (increasing rate) which corresponds to the following formula:

$$IR = HR + L3 - DR$$

The input voltage to the voltage controlled oscillator will thus behave as the inverse of the integrator output voltage.

Using the overdriver of FIG. 7, initiation of treatment for tachycardia-type arrhythmias is initiated by the patient in essentially the same manner as with the version of FIG. 6, that is, the housing 25 is placed over the implanted stimulating device so that the magnet 27 causes the implanted device to switch from an inhibit mode to a synchronous mode and the initiation pushbutton is operated. However, as the sensitivity of the implanted device is simultaneously reduced, no pulses should be generated by the implanted device synchronously with naturally occurring heartbeats. Rather, the implanted device should slave solely to the external overdriver. Thus, when the initiating pushbutton 31 is pressed, the external overdriver circuitry will generate the preselected regime of control pulses and the implanted device will track or mimic these control pulses with stimulating pulses applied to the heart itself.

While finger contacts on the external overdriver are the usually preferred method of applying signals to be tracked by the implanted device, chest electrodes may be more appropriate where the pacing vector is mostly perpendicular to the line between the shoulders.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. A system for cardiac treatment comprising:

an implantable pacer including circuit means having alternately a normal standby nontriggered demand pacing mode and a temporary triggered stimulation mode, said pacer being provided with a lead for electrically coupling said circuit means to the heart of a patient within whom the pacer is implanted, said circuit means including means for sensing electrical signals around the heart and means for providing electrical pulses suitable for stimulating the heart, said circuit means being operative in said standby mode to selectively provide inhibited stimulation of a patient's heart and operative in said triggered mode to provide nondelayed stimulation in substantial synchronism with sensed electrical trigger signals, said pacer including magnetically operable switch means for transferring said circuitry between said standby mode and said triggered mode; and an external controller for selective temporary use in conjunction with said implantable pacer, said controller including means for generating a magnetic field suitable for operating said switch means and including also signal generating circuit means for applying, to a patient, pulsating electrical trigger signals which can be sensed by the implantable pacer circuitry when operating in said triggered mode, whereby said implantable pacer will normally operate independently in a standby mode but, upon application of said controller, will operate in a triggered mode which can be manipulated externally to treat arrhythmias.

2. A cardiac pacing system comprising:

A. a fully implantable, battery powered stimulating unit having:
 a lead for establishing an electrical connection to a patient's heart;
 pulse generator means for applying stimulating pulses through said lead;
 electric signal sensing means interconnected with said lead and responsive to electrical signals received therethrough;
 a magnetic sensor;
 control circuit means for selectively operating said pulse generator, said control circuit means being responsive to said sensor for switching from a normal standby nontriggered demand pacing mode to a temporary triggered stimulation mode during the presence of a magnetic field, said control circuit means in said standby mode operating said pulse generator means in a nontriggered inhibit mode responsive to naturally occurring heartbeats and, in said triggered mode, operating said pulse generator means in a synchronous mode in which stimulating pulses are generated essentially immediately upon sensing electrical trigger signals through said lead; and B. an external unit including means providing a magnetic field for operating said sensor and means for applying, externally of a patient, electrical pulses for triggering said sensing means, whereby tachycardia type arrhythmias may be treated by externally selectable stimulation patterns by applying said external unit and bradycardia type arrhythmias are treated by said implantable unit alone in the standby mode.

3. A cardiac pacing system comprising:
A. a fully implantable, battery powered stimulating unit including:
  a lead for establishing an electrical connection to a patient's heart;
  pulse generator means for applying stimulating pulses through said lead;
  electric signal sensing means interconnected with said lead and responsive to electrical signals received therethrough;
  a magnetic sensor;
  control circuit means for selectively operating said pulse generator means, said control circuit means being responsive to said sensor for switching from a normal standby nontriggered demand pacing mode to a temporary triggered stimulation mode during the presence of a magnetic field, said control circuit means in said standby mode operating said pulse generator means in a nontriggered inhibit mode responsive to naturally occurring heartbeats and, in said triggered mode, operating said pulse generator means in a synchronous mode in which stimulating pulses are generated essentially immediately upon sensing electrical trigger signals through said lead means; and
B. an external unit comprising a hand-held package having magnetic field means for actuating said sensor, spaced finger contacts on said package, a manually actuable switch adjacent one of said contacts, and pulse generating circuits means responsive to actuation of said switch for applying between said finger contacts a predetermined sequence of electrical pulses which can be tracked by said implanted unit thereby to cause said implanted unit to generate a corresponding sequence of triggered stimulating pulses.

4. A pacing system as set forth in claim 3 wherein said finger contacts comprises a conductive, pile type material.

5. The pacing system as set forth in claim 3, wherein said pulse generating circuit means includes detector means enabled by actuation of said switch and responsive to electrical signals indicative of stimulating pulses from said implantable unit picked up via said finger contacts for initiating said predetermined sequence of pulses at a timed interval after the next cardiac triggered stimulation pulse following actuation of said switch.

6. The pacing systemm as set forth in claim 5, wherein said package also has means for disabling said detector means on the occurrence of the first pulse in said predetermined sequence.

7. The pacing system as set forth in claim 3, wherein said signal sensing means in said implantable unit has sensitivity determining means responsive to said sensor for switching from normal sensitivity in the standby mode to reduced nonzero sensitivity in the triggered mode during the presence of a magnetic field, whereby the implantable unit is converted from the inhibited standby pacing mode to a synchronous triggered mode in which stimulation pulses are triggered by the external unit but not by natural cardiac activity.

8. The pacing system as set forth in claim 3, wherein said package is elongate, said finger contacts include a pair of insulating ring-like strips with an electrically conductive outer surface affixed to said package parallel to and substantially surrounding the long axis thereof at opposite ends of said package, said switch being located between said strips at a position within reach of a finger of a hand gripping the adjacent strip.

9. The pacing system as set forth in claim 8, wherein said magnetic field means is a permanent magnet mounted in said package midway between said strips, whereby while gripping the strips with the fingers of the respective hands, the patient may center the magnet means over the site of the implanted unit and then actuate the switch.

10. The pacing system as set forth in claim 8, wherein said package is made of an electrically insulating material.

11. The pacing system as set forth in claim 8, wherein said strips are made of a conductive pile material.

12. A cardiac pacing system comprising:
A. a fully implantable, battery powered stimulating unit having:
  a lead for establishing an electrical connection to a patient's heart;
  pulse generator means for applying stimulating pulses through said lead;
  an oscillator;
  timing counter, means driven by said oscillator for activating said pulse generator at a predetermined count;
  electric signal sensing means interconnected with said lead and responsive to electrical signals received therethrough;
  a magnetic sensor;
  control circuit means for selectively resetting said counter in response to sensed electrical signals, said control circuit means being responsive to said sensor for switching from a normal standby nontriggered pacing mode to a temporary triggered stimulation mode during the presence of a magnetic field, said control circuit means in said standby mode operating to reset said counter means without activating said pulse generator and, in said triggered mode, operating to reset said counter means and essentially simultaneously activating said pulse generator means upon sensing electrical trigger signals through said lead; and
B. an external unit including means providing a magnetic field for operating said sensor and means for applying, externally of a patient, electrical pulses for triggering said sensing means,
whereby tachycardia type arrhythmias may be treated by externally selectable stimulation patterns by applying said external unit and bradycardia type arrhythmias are treated by said implantable unit alone in the standby mode.

* * * * *